(12) United States Patent  (10) Patent No.: US 6,540,762 B1
Bertling                    (45) Date of Patent:    Apr. 1, 2003

(54) DEVICE FOR PERFORATING SKIN

(75) Inventor: Wolf Bertling, Erlangen (DE)

(73) Assignee: November Aktiengesellschaft Gesellschaft fur Molekulare Medizin, Erlangen (DE)

( * ) Notice: Subject to any disclaimer, the term of this patent is extended or adjusted under 35 U.S.C. 154(b) by 0 days.

(21) Appl. No.: 09/743,235
(22) PCT Filed: Jul. 7, 1999
(86) PCT No.: PCT/DE99/02092
  § 371 (c)(1),
  (2), (4) Date: Jan. 8, 2001
(87) PCT Pub. No.: WO00/02482
  PCT Pub. Date: Jan. 20, 2000

(30) Foreign Application Priority Data

Jul. 9, 1998 (DE) .......................... 198 30 604

(51) Int. Cl.⁷ ............................... A61B 17/34
(52) U.S. Cl. ...................................... 606/182
(58) Field of Search ............... 606/1, 181, 182, 606/183, 184, 185; 600/583

(56) References Cited

U.S. PATENT DOCUMENTS

| 4,990,154 A | * | 2/1991 | Brown et al. ............... 606/182 |
| 5,147,375 A |   | 9/1992 | Sullivan et al. |
| 5,350,392 A |   | 9/1994 | Purcell et al. |
| 5,871,494 A | * | 2/1999 | Simons et al. ............... 606/182 |
| 5,873,887 A | * | 2/1999 | King et al. ................. 606/182 |
| 6,210,420 B1 | * | 4/2001 | Mauze et al. ............... 606/181 |

FOREIGN PATENT DOCUMENTS

| DE | 43 20 463 A1 | 12/1994 |
| EP | 0 255 338 A2 | 2/1988 |
| EP | 0 403 873 A1 | 12/1990 |

* cited by examiner

Primary Examiner—George R. Evanisko
(74) Attorney, Agent, or Firm—Rankin, Hill, Porter & Clark LLP

(57) ABSTRACT

A method for perforating skin including a lancet (1) held in a lancet holder (2) which, by means of a spring-loaded element (9), can be locked in a housing and moved out of the housing. To improve hygiene the invention provides for the lancet holder to be housed in a cup (5), which can be attached to the housing (8), and slidably guided in the cup.

17 Claims, 5 Drawing Sheets

DEVICE FOR PERFORATING SKIN

BACKGROUND OF THE INVENTION

1. Field of the Invention

The invention generally relates to a device for the perforation of skin and, more specifically, toward such a device that includes a lancet that is received in a housing and mounted to a spring-loaded lancet carrier.

2. Description of Related Art

Such a device is known in the prior art by the product name "Lanzer-5" from Becton Dickinson, Oxford OX4 3LY, United Kingdom, or from EP 0 061 102. The known device is composed of a multiplicity of individual parts. It also has the disadvantage that blood may accumulate in a cap, which is intended for reuse and can be screwed onto the housing. Such blood accumulations are not acceptable for hygienic reasons. It is conceivable, furthermore, that impurities such as skin diseases may adhere to the outside of the cap and, therefore, transferred from one patient to the next.

In devices known from EP 0 838 195 A1 and from U.S. Pat. No. 4,653,513, the lancet carrier extends from the housing into a cap attached to the latter. The purpose of these devices is to draw or suction blood into the cap. Such devices are complicated, since a vacuum for suctioning the blood has to be generated with them. The devices must have a correspondingly leak-tight design.

U.S. Pat. No. 4,375,815 discloses an automatically retractable lancet device that is designed as a disposable part. When the device is thrown away, parts that could still be used, from a hygienic point of view, are also thrown away. The device is relatively costly, and causes unnecessary environmental pollution.

FR 2 508 305, DE 89 00 203 U1, DE Patent 459 483 and DE Patent 355 891, which relate to the technological background of the invention, are directed toward devices for the extraction of blood samples, in which there is no removable cap provided.

SUMMARY OF THE INVENTION

An object of the invention is to eliminate the disadvantages of the prior art. In particular, the present invention provides a device for the perforation of skin that can be produced simply, is as cost-effectively as possible, and can be operated hygienically.

According to the invention, a lancet carrier is guided displaceably in a cap capable of being fastened to the housing. It is thereby possible to design the cap and lancet carrier as disposable articles. All the parts coming into contact with the patient are thrown away after the skin has been perforated, allowing the device to be operated hygienically.

Advantageously, the lancet carrier rotationally symmetrical, and preferably has a piston-like first portion. The lancet may be provided at one end of the lancet carrier and a flange-like, radially continuous projection may be provided at the other end. Such a lancet carrier can be produced simply.

In further accordance with the present invention, the lancet carrier is guided in the cap in a corresponding cylindrically designed second portion. The cap expediently has a first orifice for connection to the housing and a second orifice for the passage of the lancet. The cap and/or the lancet carrier may be produced from injection-molded plastic. The second orifice may be closed by means of a plastic film that is preferably injected-molded on in one piece, thereby insuring that the lancet is not contaminated before use.

The cap is affixed to the housing, for example, by means of a bayonet fastening, a locking connection, or a thread. A simple fastening is thereby produced.

The element is advantageously designed such that, with the cap removed, the element can be pressed, against the biasing force of a spring, into the housing up to a prestressed first position and can be automatically interlocked there. By at least one button being actuated the interlock can be released, so that the element is moved into a second position. A particularly simple and cost-effective makeup of the device becomes possible as a result.

In the second position, expediently, a locking or clamping element provided on the element is interlocked or clamped together with a corresponding counter-locking or counter-clamping element provided at the other end of the lancet carrier. The lancet advantageously passes through the plastic film and projects beyond the circumferential edge of the second orifice.

During the removal of the cap, with lancet extended, from the housing, the lancet carrier can be retracted up to a stop by means of the element. After the lancet carrier rests against the stop, the connection formed between the locking or clamping element and the counter-locking or counter-clamping element is released. With the cap then having to be thrown away, the risk of injury by a lancet projecting beyond the edge of the second orifice is avoided.

For a further simplification of the device in terms of production, the element may also be produced from injection-molded plastic. Expediently, a locking spring is injection-molded on the element in a one-piece design.

In further accordance with the present invention, the element may be guided displaceably in a carrying element received in the housing. In this case, the spring is advantageously supported against a bottom of the carrying element, while a prolongation, which extends from the element, can engage through a bottom perforation a design corresponding to the prolongation and can be secured by a dovetailed means against passage through the perforation. The above-mentioned features make it easier to assemble the device.

The carrying element expediently extends over the circumferential edge of the housing, so that the cap can be slipped onto the carrying element.

BRIEF DESCRIPTION OF THE DRAWINGS

Exemplary embodiments of the invention are explained in more detail by means of the drawings, wherein.

DETAILED DESCRIPTION OF THE PREFERRED EMBODIMENTS

Figure 1:
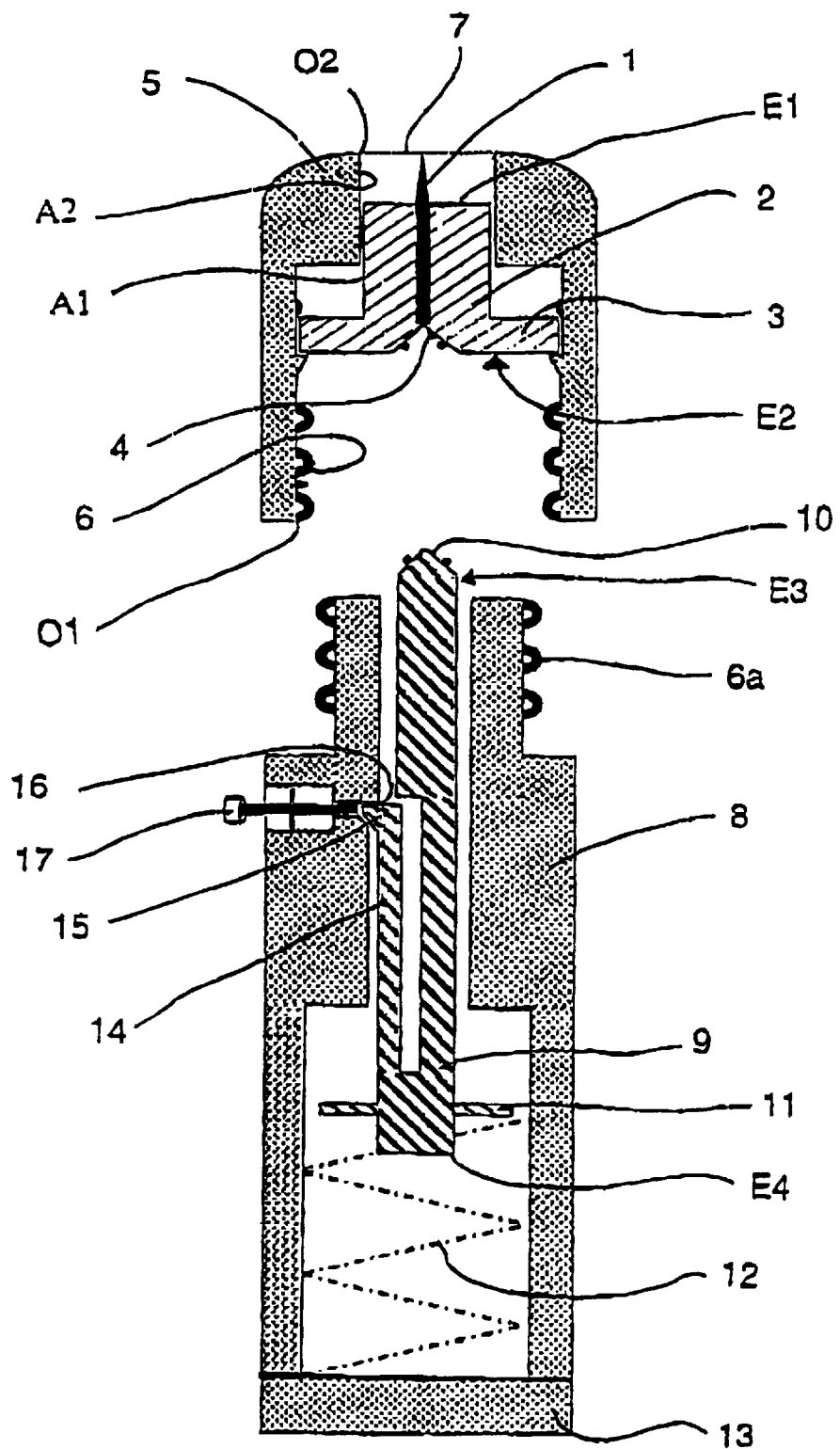
FIG. 1 shows a diagrammatic cross-sectional view of a first device, with the cap removed.

In FIG. 1, a lancet 1 produced from metal is received at one end E1 of a lancet carrier 2. The lancet carrier 2 has a rotationally symmetric design and has, at its other end E2, a flange-like projection 3 and a V-shaped recess 4. The lancet carrier 2 is expediently produced from plastic. It is guided with a piston-like first portion A1 in a corresponding cylindrically designed second portion A2 of a cap 5. An internal thread 6 is provided in the vicinity of a first orifice O1 on the inner wall of the cap 5. A second orifice O2 is closed by means of a plastic film 7. The plastic film 7 is expediently injection-molded onto the cap 5 in a one-piece design.

An element 9 is displaceably received in a housing 8. Located at a first end E3 of the element 9 is a point 10 corresponding to the V-shaped recess 4. In the vicinity of a second end E4 of the element 9 is provided a further radially continuous projection 11. Supported on the projection 11 is a spring 12, which rests with its opposite end against the housing closure 13. The element 9 is expediently produced from plastic, and has a locking spring 14 in a one-piece design. In the tensioned state shown in FIG. 1, a first locking element 15 engages into a perforation 16 provided on the housing 9. The first locking element 15 is capable of being pressed down by means of a button 17. An external thread 6a is provided by the housing 8, and corresponds to the internal thread 6.

Figure 2:
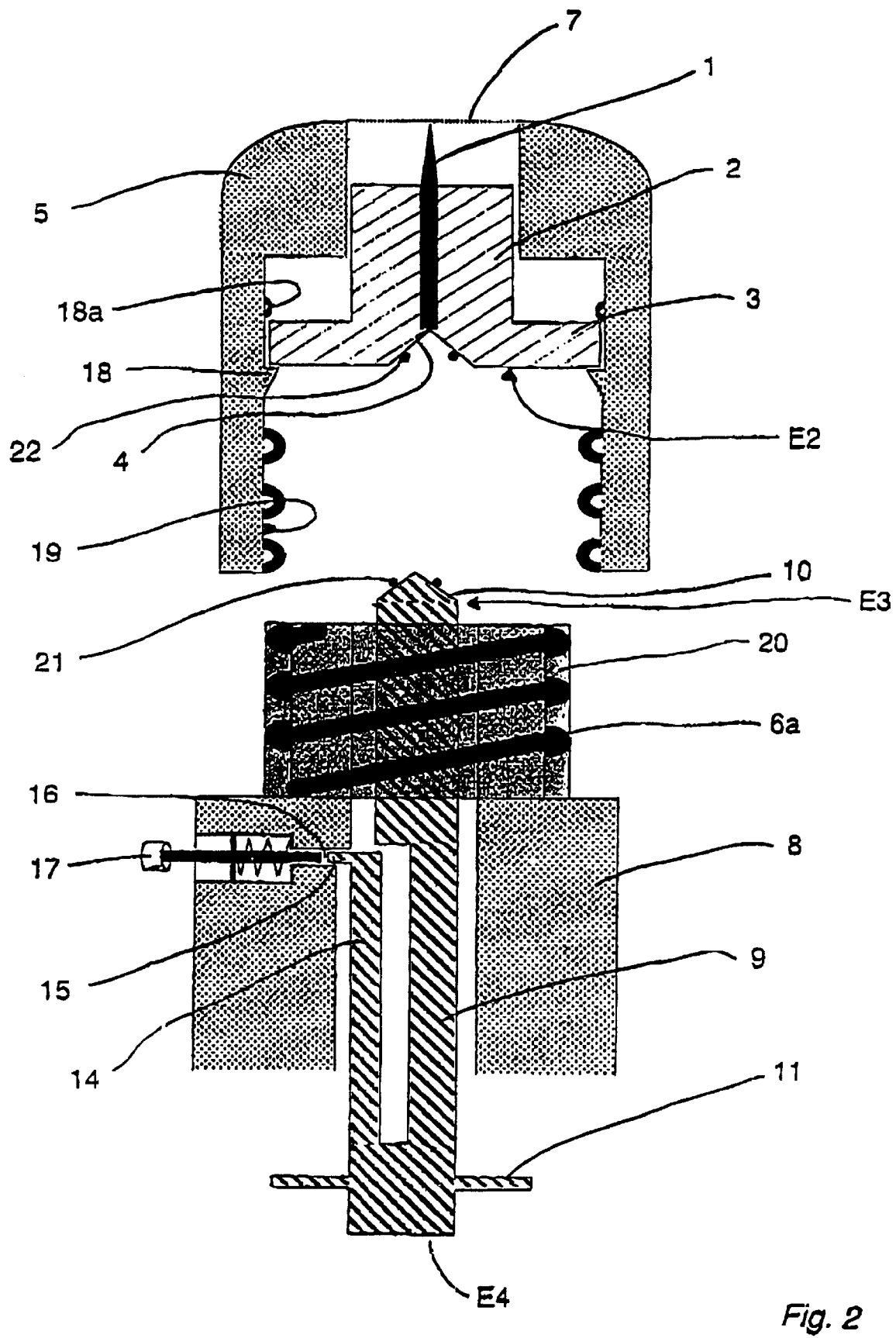
FIG. 2 shows a diagrammatic cross-sectional view of the cap and a partial side view of the housing according to FIG. 1.

FIG. 2 shows the cap 5, intended as a disposable article, with the lancet carrier 2 received therein. Injection-molded on the inner wall of the cap 5 are a plurality of snap hooks 18, which prevent the inserted lancet carrier 2 from falling out. First bosses 18a hold the lancet carrier 2 in a retracted position and prevent the plastic film 7 from being unintentionally pierced. At least one second boss 19 is provided in the valley of an outer thread flight of the internal thread 6. A portion of the housing 8 is shown in a side view. A plurality of recesses 20 corresponding to the second boss 19 are provided on the ridge of an outer thread flight of the external thread 6a.

A bead 21 provided on the point 10 is designed such that it is capable of being interlocked with prolongations 22 injection-molded in the V-shaped recess.

Figure 3:
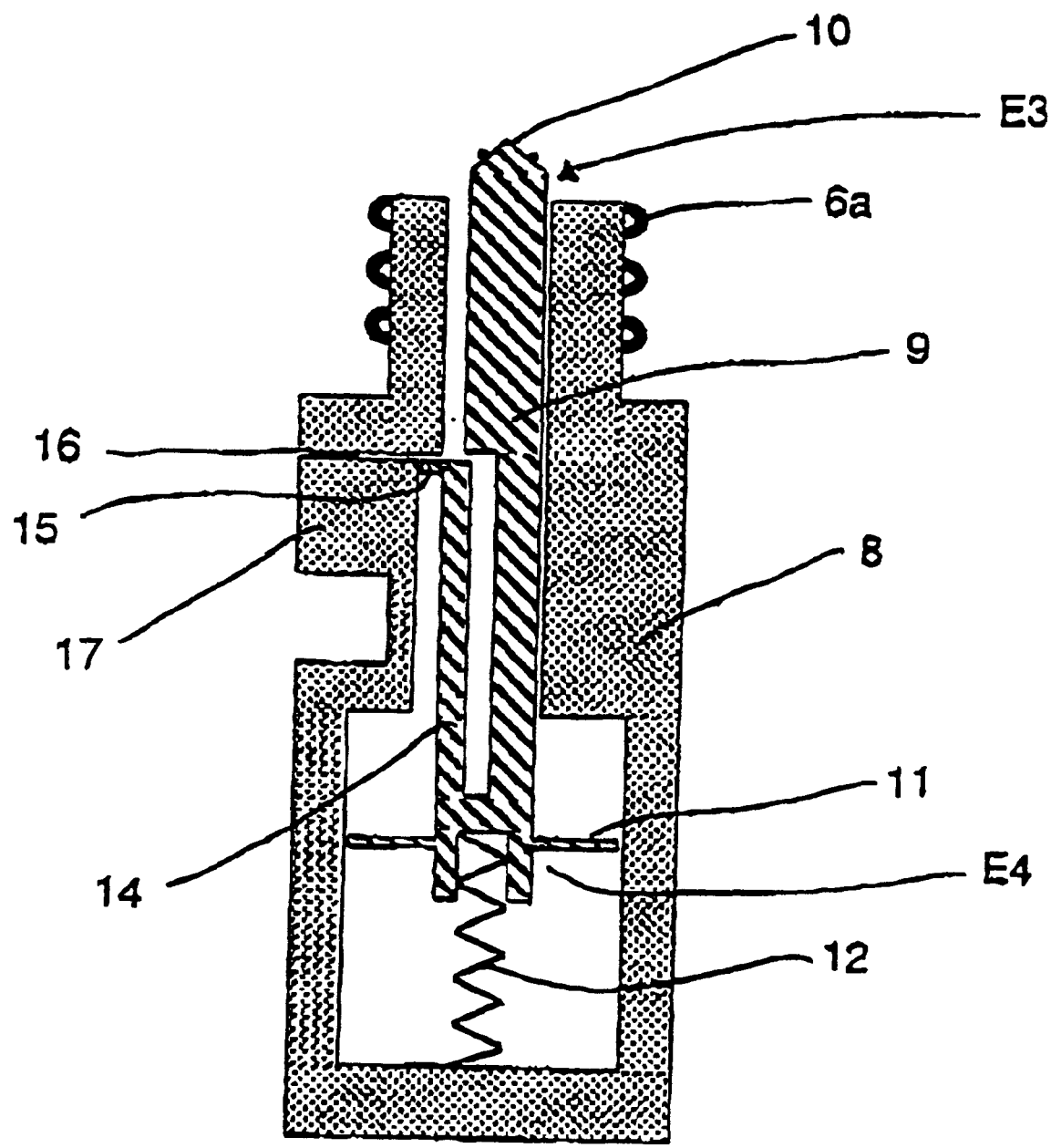
FIG. 3 shows a diagrammatic cross-sectional view of the housing of a second device.
Figure 4A:
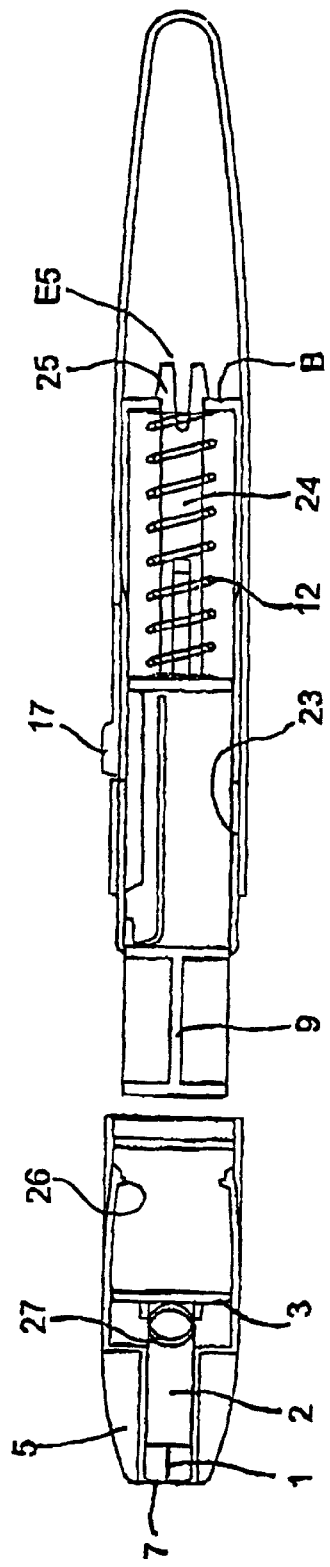
FIGS. 4a–f show the functioning of a third device in a diagrammatic cross-sectional view.
Figure 4B:
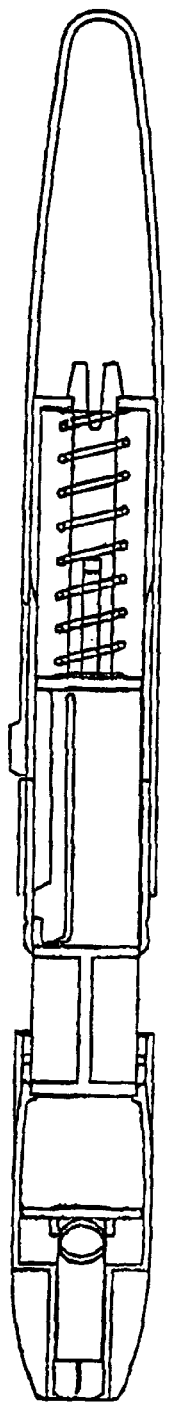
Figure 4C:
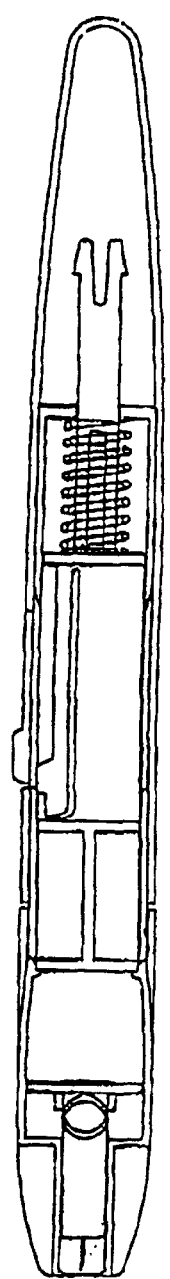
Figure 4D:
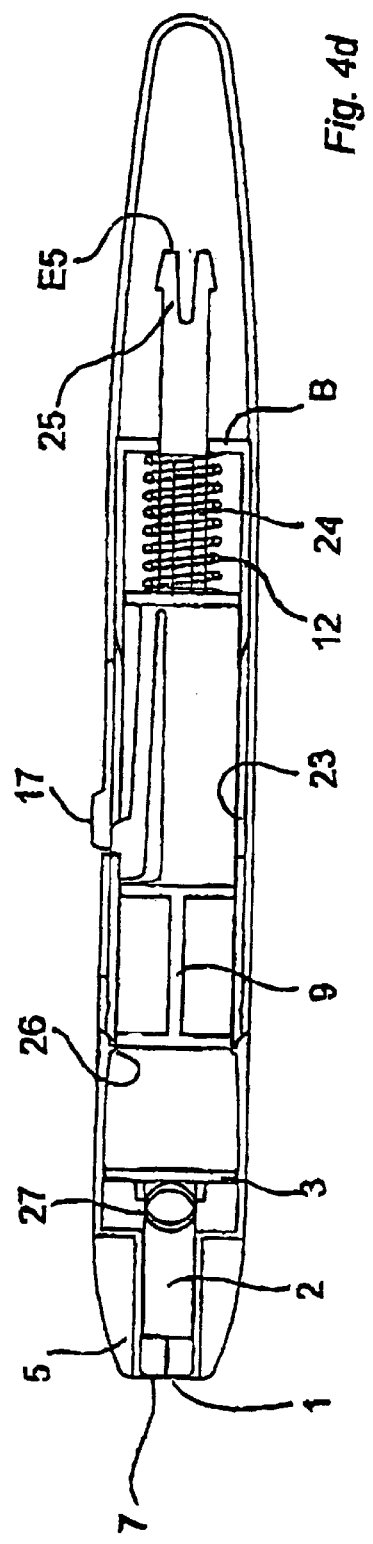
Figure 4E:
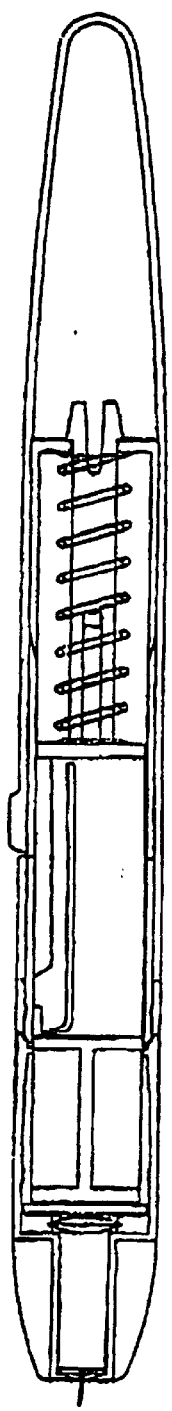
Figure 4F:
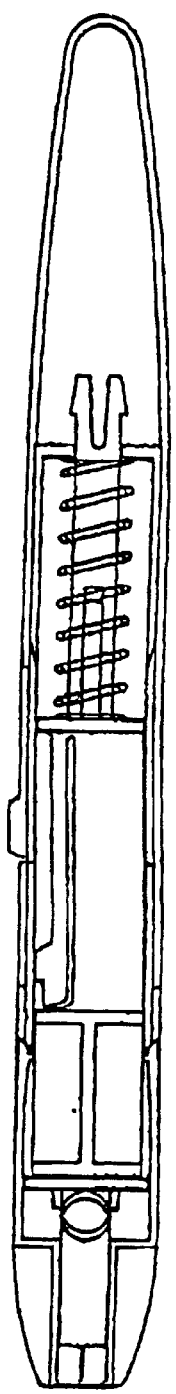

FIG. 3 shows the housing 8 according to a second embodiment of the present invention. Here, the further projection 11 is formed from flexible tongues, which, for assembly, make it possible to push the element 9 in through the housing orifice. The provision of a housing closure 13 may be dispensed with here. In a further simplification in terms of production, the button 17 is designed as a spring element injection-molded in one piece onto the housing 8.

In the third embodiment shown in FIGS. 4a–f, a carrying element 23, in which the element 9 is received, is built into the housing 8. A strip-like prolongation 24 extends from the element 9. The free end E5 of the prolongation is designed as a dovetailed locking means 25, which engages behind a further perforation provided in the bottom B of the carrying element 23. The spring 12 is supported, on the one hand, against the bottom B and, on the other hand, against the lancet carrier 2 designed here in the manner of a double piston.

The cap 5 has at least two further locking springs 26 projecting radially inward. The lancet carrier 2 is provided, on the side facing the lancet 1, with spring elements designed in the form of elastic plastic rings 27.

The devices function as follows:

The device shown in FIGS. 1 to 3 is tensioned by the element 9 being pressed in counter to the force generated by the spring 12. At the same time, the locking element 15 snaps into the perforation 16 or behind an edge formed in the vicinity of the perforation 16 and thus prevents the element 9 from reemerging from the housing 8. The cap 5 is subsequently screwed onto the housing 8. The exit travel of the lancet 1 and therefore the pricking depth can be predetermined by the screw-in depth of the cap 5 on the housing 8. The predetermined pricking depth is indicated by the interaction of the second boss 19 with the recesses 20 as a result of a locking of the second boss 9 into one of the recesses 20 when the cap 8 is screwed in.

After the desired pricking depth is set, the device is placed with the second orifice O2, for example, onto the finger of the patient and the button 17 is pressed. As a result of this, the element 9 presses abruptly onto the lancet carrier 2. The lancet 1 pierces the plastic film 7 and perforates the skin to the desired pricking depth.

At the same time, the first end E3 of the element 9 is interlocked with the V-shaped recess 4. The interlock is achieved in that the V-shaped recess 4 has injection-molded on it a continuous bead 21, which corresponds to prolongations 22 at the first end E3 of the element 9. It is also conceivable, however, for the first end E3 to be designed with a more obtuse angle than the angle of the V-shaped recess 4. In this case, a clamping connection is made between the first end E3 and the V-shaped recess 4.

After perforation, the cap 5 is unscrewed from the housing 8. At the same time, the lancet carrier 2 is dragged back into its initial position and is held there between the first boss 18a and the snap hooks 18. The lancet 1 then no longer projects beyond the second orifice O2. Undesirable injuries therefore cannot occur. After the cap 5 has been unscrewed, the locking or clamping connection formed between the first end E3 and the V-shaped recess 4 is released by means of a slight pull. The cap 5 is thrown away together with the lancet carrier 3.

The cap 5 may also be interlocked on the housing 8. In this case, the pricking depth may be varied by the provision of caps 5 of different geometry and/or lancets 1 of different length.

FIGS. 4a–f show the functioning of the third embodiment of the invention. When the cap 5 is placed onto the housing 8, the element 9 first comes with its front piston into bearing contact with the further locking elements 26. The cap 5 is then pressed against the housing 8 counter to the spring force of the spring 12, until the locking element 15 locks into the perforation 16. At the same time, the further locking elements 26 are spread apart from one another by that part of the carrying element 23 that projects from the housing 8, so that the element 9 can be moved toward the lancet carrier 2. When the mechanism is triggered by the button 17 being pressed down, the lancet 1 is driven abruptly through the plastic film 7. It is then retracted into the cap 5 again as a result of the spring action of the elastic plastic rings 27, with the result that the risk of injuries on used caps is reduced.

What is claimed is:

1. A device for perforation of skin, said device comprising a lancet (1), a lancet carrier (2), a housing (8), an element (9), a cap (5), a biasing spring (12), and a plastic film (7), said lancet (1) being received on said lancet carrier (2), said lancet, by operation of said element (9), being adapted to extend from said housing (8), said element being lockable in the housing (8) under prestress of said biasing spring (12), said lancet carrier (2) being displaceably received in the cap (5), and said cap being capable of being fastened to the housing (8), wherein the lancet carrier (2) includes a piston-like first portion (A1) that serves to guide the lancet carrier in the cap (5), and said cap (5) defines a first orifice (O1) and a second orifice (O2), said first orifice being connected to the housing (8) and the second orifice (O2) comprises the plastic film closing said second orifice and through which said lancet passes, said plastic film (7) being injection-molded on in one piece with the cap.

2. The device according to claim 1, wherein the lancet carrier (2) has a rotationally symmetric design.

3. The device according to claim 1, wherein the lancet (1) is disposed at one end (E1) of the lancet carrier (2) and a flange-like radially continuous projection (3) is at the other end (E2) of the lancet carrier.

4. The device according to claim 1, wherein the cap (5) has a second portion (A2) that is cylindrically-shaped and dimensioned to guide the lancet carrier (2) therein.

5. The device according to claim 1, wherein at least one of the cap (5) and the lancet carrier (2) is made from injection-molded plastic.

6. The device according to claim 1, wherein the cap (5) is adapted to be secured to the housing (8) by one of a bayonet fastening, a locking connection and a thread (6, 6a).

7. The device according to claim 1, wherein the cap may be removed from the housing and, when the cap (5) is removed, the element (9) may be pressed, counter to the force of the biasing spring (12), into the housing (8) up to a prestressed first position and automatically interlocked there by locking means.

8. The device according to claim 7, wherein said locking means comprises at least one button (17), said at least one button being adapted to release the element from the housing, so that the element (9) can be put into a second position.

9. The device according to claim 8, wherein, in the second position, a locking or clamping element (10, 22) provided on the element is interlocked or clamped together with a corresponding counter-locking or counter-clamping element (4, 21) provided at the other end (E2) of the lancet carrier (2), and the lancet (1) passes through the plastic film (7) and projects beyond a circumferential edge of the second orifice (02).

10. The device according to claim 1, further comprising a locking spring (14, 15), said locking spring being injection-molded on the element (9) and serving to lock the element to the housing.

11. The device according to claim 1, further comprising a carrying element (23) that is received in the housing (8), said carrying element (23) serving to displaceably guide the element (9).

12. The device according to claim 11, wherein the biasing spring (12) is supported against a bottom (B) of the carrying element (23).

13. The device according to claim 12, further comprising a prolongation (24) extending from the element (9), said prolongation extending through a perforation in said carrying element bottom (B) and engaging said carrying element bottom (B), wherein the perforation has a cross-sectional shape corresponding to a shape of said prolongation, and wherein said prolongation is secured, by operation of a dovetailed locking means (25), against passage through the perforation.

14. The device according to claim 11, further comprising a prolongation (24) extending from the element (9), said prolongation extending through a perforation in said carrying element bottom (B) and engaging said carrying element bottom (B), wherein the perforation has a cross-sectional shape corresponding to a shape of said prolongation, and wherein said prolongation is secured, by operation of a dovetailed locking means (25), against passage through the perforation.

15. The device according to claim 11, wherein the carrying element (23) extends over a circumferential edge of the housing (8), so that the cap (5) can be slipped onto said carrying element.

16. A device for perforation of skin, said device comprising a lancet (1), a lancet carrier (2), a housing (8), an element (9), a cap (5), a biasing spring (12), and a stop (18) in said cap, said lancet being received on the lancet carrier (2) * and being adapted to extend from the housing (8) by operation of said element (9), said element being lockable in the housing (8) under prestress of said biasing spring (12), said lancet carrier (2) being displaceably received in the cap (5), and said cap being removably attached to the housing (8), wherein the lancet carrier (2) includes a piston-like first portion (A1) that serves to guide the lancet carrier in the cap (5) and, wherein, when the cap is removed from the housing (8) with lancet (1) extended, the element (9) is configured to retract the lancet carrier (2) up to the stop (18).

17. The device according to claim 16, wherein the element (9) is made from injection-molded plastic.

* * * * *